(12) United States Patent
Zander

(10) Patent No.: US 6,299,592 B1
(45) Date of Patent: *Oct. 9, 2001

(54) LAPAROSCOPIC INSUFFLATOR

(75) Inventor: Charles Zander, Buffalo Grove, IL (US)

(73) Assignee: Northgate Technologies Inc., Elgin, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,810

(22) Filed: Oct. 16, 1998

Related U.S. Application Data

(63) Continuation-in-part of application No. 09/052,459, filed on Mar. 31, 1998, now abandoned.

(51) Int. Cl.[7] .............................. A61M 37/00; A61B 5/00
(52) U.S. Cl. ............................................ 604/26; 600/560
(58) Field of Search ..................... 604/23–26; 600/560

(56) References Cited

U.S. PATENT DOCUMENTS

| | | | | |
|---|---|---|---|---|
| 5,013,294 | * | 5/1991 | Baier ....................................... | 604/26 |
| 5,246,419 | | 9/1993 | Absten . | |
| 5,292,304 | * | 3/1994 | Mantell et al. ......................... | 604/26 |
| 5,328,458 | * | 7/1994 | Sekino et al. .......................... | 604/23 |
| 5,423,741 | * | 6/1995 | Frank ..................................... | 604/23 |
| 5,439,441 | * | 8/1995 | Grimsley et al. ...................... | 604/26 |
| 5,549,546 | * | 8/1996 | Schneider et al. .................... | 604/26 |
| 5,676,155 | * | 10/1997 | Novak et al. ......................... | 128/747 |
| 5,814,012 | * | 9/1998 | Fleenor et al. ........................ | 604/26 |
| 5,908,402 | * | 6/1999 | Blythe ................................... | 604/26 |

OTHER PUBLICATIONS

UCSD HealthGuide, "Laparoscopy" http://vcdean98–27.ucsd.edu/guide/T0255.htm, Mar. 23, 1998.
AAG CH E—Products—EC Laparoscopy, "Modular trocar generation with silicone valve" http://www.aesculap.de/e/chir/chp_mtro.htm, Mar. 23, 1998.
AAG CH E—Products—EC, "Gasless laparoscopy The concept/technique" http://www.aesculap.de/e/chir/chp_tech.htm, Mar. 23, 1998.
Laparascopy.com—Welcome page http://www.laparoscopy.com/welcome.html, Mar. 23, 1998.
"Computerized Insufflation," advertisement by Snowden–Pencer. While the date of the advertisement is unknown, it is believed that the advertisement was available to the public prior to Mar. 31, 1998.

* cited by examiner

*Primary Examiner*—Sharon Kennedy
(74) *Attorney, Agent, or Firm*—Brinks Hofer Gilson & Lione

(57) ABSTRACT

A system, apparatus, and method for supplying continuous and intermittent insufflating gas flow are disclosed. The system, apparatus, and method is capable of providing a continuous flow (100% duty cycle) of insufflation gas, while assuring the continuity of the delivery lines, and the pressure sense lines. The disclosure describes a delivery assembly, an internal sensing assembly, an internal sense line, a pressure assembly, and a controller.

50 Claims, 4 Drawing Sheets

FRONT PANEL CONTROLS

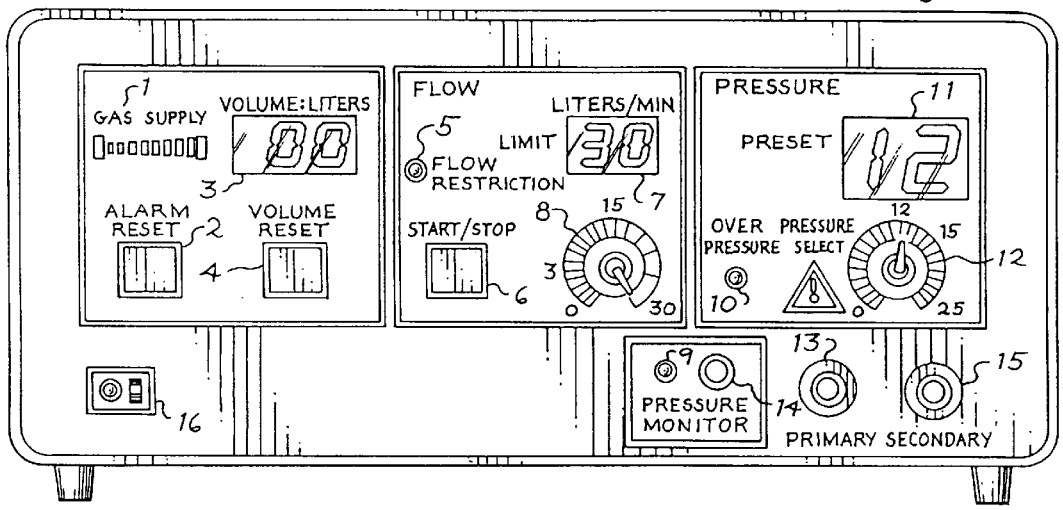

Fig. 2

FRONT PANEL CONTROLS

[1] GAS SUPPLY INDICATORS
Three colors of LED to indicate the amount of gas available.

NOTE: Do not start a procedure with less than 125 PSI tank pressure, or less than 50 PSI central supply pressure.

[2] ALARM RESET PUSH BUTTON
Momentarily silences the audible alarm.

[3] VOLUME DISPLAY
Indicates the total amount of gas used.

[4] VOLUME RESET PUSH BUTTON
Clears the volume display to zero.

[5] FLOW RESTRICTION INDICATOR
This yellow LED turns on when the unit senses a high restriction in the gas path.

[6] START/STOP PUSH BUTTON
Starts or stops the flow of gas.

[7] FLOW CONTROL DISPLAY
When the word ACTUAL is lit, the display indicates the actual flow rate. When the flow limit adjustment is made, the word LIMIT is lit and the display indicates the maximum flow rate allowable.

[8] FLOW LIMIT DIAL
Allows the user to select the maximum flow rate from 0 to 30 liters per minute.

[9] PATIENT PRESSURE MONITOR INDICATOR
This green LED is active any time the external pressure sense line is in use.

[10] OVER PRESSURE INDICATOR
This red LED turns on anytime the pressure exceeds the preselected pressure setting by 2 mmHg or more.

[11] PRESSURE DISPLAY
When the work ACTUAL is lit, the display indicates the actual abdominal pressure. When the pressure select adjustment is made, the word PRESET is lit and the display indicates the preset pressure.

[12] PRESSURE SELECT DIAL
Allows the user to select the maximum pressure. Range is from 0 to 25 mmHg.

[13] PRIMARY GAS OUTPUT TO PATIENT
Connector for patient tubing set.

[14] PATIENT PRESSURE MONITOR CONNECTOR
Connector for external pressure monitoring tubing set.

[15] SECONDARY GAS OUTPUT TO PATIENT
Connector for patient tubing set.

[16] POWER SWITCH
Turns the power on and off to the unit.

LAPAROSCOPIC INSUFFLATOR

REFERENCE TO RELATED APPLICATION

The present application is a continuation-in-part of Ser. No. 09/052,549, filed Mar. 31, 1998, now abandoned the entire disclosure of which is hereby incorporated by reference.

BACKGROUND OF THE INVENTION

The present invention relates to the field of surgical instruments, and in particular, relates to the technology and instrumentation used to achieve pneumoperitoneum during laparoscopy and laparoscopic surgery.

Surgeons have used laparoscopic surgery to perform a variety of procedures. By manipulating laparoscopes and video telescopes, surgeons gain a visualization of the abdominal cavity while minimizing tissue and muscle injury that normally accompanies conventional invasive procedures. Compared to conventional surgery, laparoscopy reduces patient trauma, decreases patient recovery time, and yields significant cost savings by reducing post-operative care.

The proper hardware and instrumentation are essential to the performance of safe laparoscopic procedures. To create a sufficient area for the introduction of a laparoscope and other instruments, the abdominal wall is first raised from the organs enclosed in the abdominal cavity. Separation is conventionally attained by pressurizing the abdominal cavity with a suitable gas. Typically, carbon dioxide is used. The presence of artificial gas in the peritoneal cavity to achieve exposure during laparoscopy is referred to as pneumoperitoneum.

Two conventional techniques are practiced to create pneumoperitoneum. One technique to provide access into the intra-abdominal cavity consists of inserting a Verres needle through the umbilicus. A Verres needle is inserted through the subumbilical area until the tip of the needle communicates with the anterior abdominal wall. When the needle is at an appropriate depth, gas is infused through a hollow section of the needle by an insufflator until the abdomen is expanded away from the organs enclosed by the abdominal cavity. Once pneumoperitoneum is achieved, typically at a pressure between twelve to fifteen millimeters of mercury, the Verres needle is withdrawn and a trocar is inserted through the umbilical wound. Laparoscopic instruments are then inserted through the cannula to provide a direct vision of the surgery.

A second technique may also be practiced to create pneumoperitoneum. The second procedure, sometimes referred to as the Hassan procedure, involves making a small incision in the umbilicus and inserting a trocar prior to insufflating the abdominal cavity. Gas is then infused through the trocar to create pneumoperitoneum. A laparoscope and endoscopic instruments are then inserted through the trocar allowing the surgeon to view, examine, and operate in the abdominal cavity.

As laparoscopic procedures often require the manipulation of several instruments including a light source and a video source, additional trocars are frequently necessary. Because the trocars are of fixed diameter, their gas infusion ports do not always permit the sufficient flow of gas to sustain the intra-abdominal pressure needed to maintain pneumoperitoneum. The infusion pressure of the insufflating gas is generally limited to forty-five millimeters of mercury. Conventional insufflators limit gas flow rates to a maximum of about twenty liters per minute. However, current laparoscopic procedures suction blood, other fluids, and smoke for brief periods requiring flow rates in excess of twenty liters per minute. Recently, thirty and forty liters per minute insufflating machines have been introduced to the laparoscopic market. These machines may require custom trocars with exceptionally large infusion ports to sustain high gas flow rates. When these trocars are not used, the machines are limited to maximum flow rates of about twenty liters per minute.

Intra-abdominal pressure may be monitored by an external sense line. One practice relies on inserting a pressure sensor directly into the intra-abdominal cavity through a gas delivery channel or by direct measurement unencumbered by gas flowing through the delivery channel. One potential disadvantage associated with using an external sense line is that it may be blocked or open because of a failed connection or an obstruction within the abdominal cavity.

A commonly used process to monitor pressure in the intra-abdominal cavity is to stop the infusion of insufflation gas into the peritoneal cavity, allow the pressure to stabilize, and then measure a static pressure. Algorithms and predictive techniques are employed to calculate the intra-abdominal pressure. The "flow and stop" process causes the gas delivered in a unit of time or duty cycle to be lower than the peak flow rate of the machine. The duty cycle limitation prevents these machines from immediately reacting to unforeseeable pressure losses and gas leakage that flow from the insertion of trocars into the intra-abdominal cavity.

In light of the strengths and weaknesses of the above equipment, there is a need for an insufflation system, apparatus, and method for performing safe laparoscopy. The system, apparatus, and method should be capable of assuring continuity from the intra-abdominal cavity and through the external sense line, facilitate static and continuous pressure measurements, provide a continuous infusion gas flow, and be capable of detecting blocked or inadvertently disconnected gas output lines. To this end, the system, apparatus, and method should be simple to operate and provide visual and audio warnings to its operator.

SUMMARY OF THE INVENTION

A system, apparatus, and method for supplying continuous and intermittent insufflating gas flow are disclosed. The system, apparatus, and method are capable of providing a continuous flow (100% duty cycle) of insufflation gas, while assuring the continuity of the delivery lines and the pressure sense lines. This disclosure describes a delivery assembly, an internal sensing assembly, an internal sense line, a pressure assembly, and a controller.

BRIEF DESCRIPTION OF THE DRAWINGS

FIG. 2 is a view of the front panel of the embodiment of FIG. 1.

DETAILED DESCRIPTION OF THE PRESENTLY PREFERRED EMBODIMENTS

Figure 1:
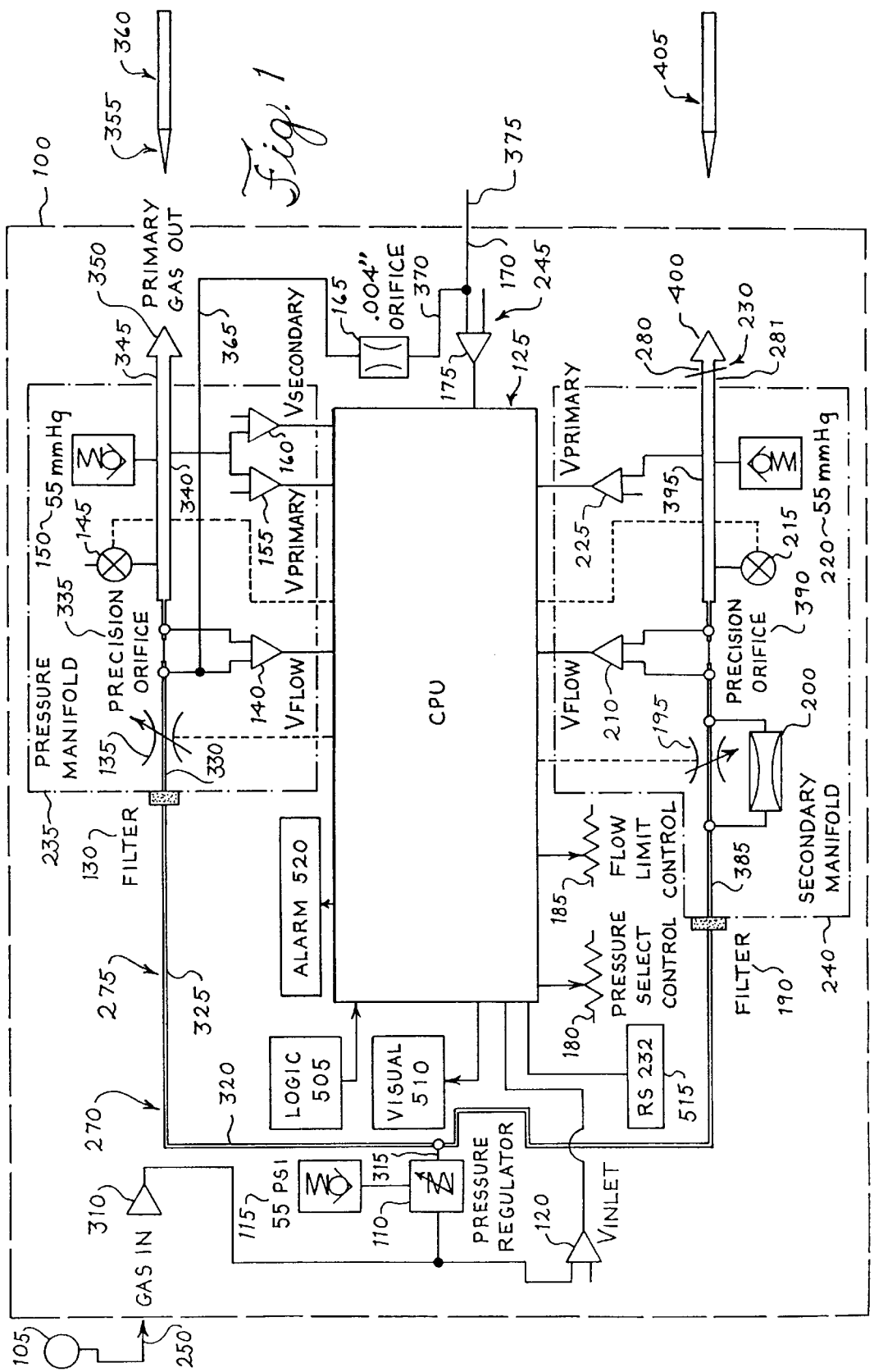
FIG. 1. is a diagram of a first embodiment of an improved laparoscopic insufflator.

In the drawings depicted elements are not necessarily drawn to scale and the same reference numbers through several views designate alike and similar elements.

I. First Embodiment

FIG. 1 shows a first embodiment of a multiple output port laparoscopic insufflator 100. The multiple output port laparoscopic insufflator 100 includes a plurality of gas delivery paths 270, primary and secondary manifolds 235 and 240, a separate sensing assembly 245, a separate sense line 170, and a controller 125. The delivery paths 270 serve to deliver insufflating gas from a pressurized source 105 to a plurality of output lines 360 and 405 which lead into the patient. Monitoring the patient's peritoneal pressure is achieved by primary internal pressure sensors 155 and 160, a secondary internal pressure sensor 225, the separate sense line 170, and the internal sensing assembly 245.

The plurality of gas delivery paths 270 include a primary gas delivery path 275 and a secondary gas delivery path 280. The primary gas path 275 includes a gas input connector 310, a common receiving channel 315, a primary branching channel 320, a primary filter delivery channel 325, a primary manifold filter 130, an input primary manifold channel 330, a primary flow control valve 135, a primary precision orifice 335, an output primary manifold channel 340, a primary gas output channel 345, and a primary gas output connector 350. The gas input connector 310 is rigidly attached to the common receiving channel 315. A pressurized source connector 250 provides an air tight junction between the pressurized source 105 and the gas input connector 310. As shown, a gas flow path to the primary manifold 235 includes the common receiving channel 315, the primary branching channel 320, and the filter delivery channel 325. The primary branching channel 320 and the filter delivery channel 325 are preferably a continuous channel to minimize insufflation gas loss. The input primary manifold channel 330 introduces insufflation gas into the primary manifold 235. The precision orifice 335 provides a gas flow path from the input primary manifold channel 330 to the output primary manifold channel 340. The output primary manifold channel 340 extends the gas flow path to the primary gas output channel 345 that terminates at the primary gas output connector 350. The primary gas output connector 350 and an external line connector 355 are designed to provide an air tight junction between the primary gas output channel 345 and an external output line 360.

FIG. 1 also shows the secondary gas delivery path 280. Because the gas delivery paths and connectors are similar or identical, the prior channel descriptions also describe the channels and connectors that define the secondary gas delivery path 280. It should be understood that although two separate gas delivery paths, 275 and 280, are shown, additional delivery paths may be added in alternative embodiments. Each delivery path would be similar or identical to the gas delivery paths 275 and 280.

The common receiving channel 315 includes a supply pressure sensor 120, a primary regulator and pressure relief valve 110 and 115, a primary filter assembly 130, and a primary manifold 235. The supply pressure sensor or pressure-measuring transducer 120 monitors gas supplied by a pressurized source 105. The pressure-measuring transducer 120 communicates with a controller or microprocessor (CPU) 125 to indicate the amount of gas available for insufflation. The primary regulator and pressure relief valves 110 and 115 monitor the delivery pressure of the common receiving channel 315 of insufflating gas. Operation of the regulator and pressure relief valves 110 and 115 are statically controlled and include a pressure regulator 110 serially connected to a static pressure relief valve 115. The pressure regulator 110 and static pressure relief valve 115 have operating values that are selected to provide a safe operating pressure for a given laparoscopic procedure. The primary filter assembly 130 is attached to the regulator and pressure relief valve 110 and 115 by a flow path formed by the common receiving channel 315, the primary branching channel 320, and the filter delivery channel 325. The filter 130 disclosed in this embodiment provides a particulate barrier down to 20 microns. As shown, the primary manifold 235 is attached to the filter assembly 130 by an air tight connection with the first input manifold channel 330. The primary manifold 235 is comprised of a primary flow control valve 135, a primary internal flow sensor 140, a plurality of primary internal pressure sensors 155 and 160, and a plurality of primary pressure relief valves 145 and 150.

FIG. 1 illustrates the components that define the primary manifold 235. The primary flow control valve 135 controls the flow of insufflation gas from the filter assembly 130 into the primary manifold 235 in response to the CPU 125. The CPU 125 communicates to the primary flow control valve 135 in response to measurements sampled from the primary and secondary internal flow sensors 140 and 210, the primary and secondary pressure sensors 155, 160, and 225, the separate sensing assembly 245, a pressure select control 180, and a flow limit control 185. The gas flow rate in the primary manifold 235 is calculated by the CPU 125 in response to the signal received from the differential flow measuring transducer 140. The differential flow measuring transducer 140 communicates the relative flow rate through the primary precision orifice 335 to the CPU 125. The primary internal pressure is sampled in the output primary manifold channel 340 by two pressure-measuring transducers 155 and 160 connected to the output primary manifold channel 340 and in communication with the CPU 125. The use of two pressure-measuring transducers 155 and 160 provide redundant pressure calculations as a safety feature.

The primary manifold 235 further includes a digitally responsive primary pressure relief valve 145 that controls the internal pressure of the primary gas output channel 345 by responding to the CPU 125. The CPU 125 communicates to the digitally responsive primary pressure relief valve 145 in response to one of two pressure-measuring transducers 155 and 160. A static pressure relief valve 150 connected to the output primary manifold channel 340 provides further redundant pressure control to the primary gas output channel 345.

Feedback channels 365 and 370 provide a gas flow path from the input primary manifold channel 330 to the internal sense line 170. The feedback channels 365 and 370 include a first feedback channel 365 and a second feedback channel 370. The first feedback channel 365 is joined to the input primary manifold channel 330 at one end and to the input junction of a feed-flow orifice 165 at another end. The second feedback channel 370 is joined to the output junction of the feed-flow orifice 165 at one end and to an internal sense line 170 that enters the separate sensing assembly 245 at another end.

The separate sensing assembly 245 is comprised of a pressure-measuring transducer 175 and a source of positive pressure which in this embodiment is provided through the feedback channels 365 and 370, and the feed-flow orifice 165. The separate sense line 375 is comprised of an enclosed hollow channel such as a hollow tube. The channel has a male and a female connector joined to opposing ends of the separate sense line 170. At one end, the separate sense line 375 is coupled to the separate sense line 170 in the separate sensing assembly 245. At the other end, the separate sense line 375 is coupled to an infusion port or a trocar inserted in the intra-abdominal cavity. The separate sense line 170 further has an air tight connector that slidably receives the second feedback channel 370 in the internal sensing assembly.

The components, channels, and connectors that define the second flow path 280 are similar to the components that define the primary flow path 275, and therefore, only the differences will be described. A bleed-off orifice 200 is connected in parallel across a secondary flow control valve 195. The bleed-off orifice 200 provides a second flow path from a secondary filter assembly 190 to a secondary precision orifice 390 and is attached to a secondary manifold channel 385 at its front and back ends.

The secondary flow path 280 also uses a single pressure-measuring transducer 225 connected to an output secondary manifold channel 395. Redundant monitoring of the secondary flow path 280 is achieved by the controller's 125 pressure comparisons of the pressure measurements sampled from the primary internal pressure sensors 155 and 160 and the pressure measurements sampled from the separate sensing assembly 245. A flap valve 230 is slidably attached between the secondary gas output channel 281 and a secondary gas output connector 400. When only the primary gas output channel 345 is engaged, the flap valve 230 is closed and blocks the secondary gas output channel 281. The closure of the secondary gas output channel 281 causes a substantial pressure build up in the output secondary manifold channel 395 from the gas flowing through the bleed-off orifice 200 connected in parallel across the closed secondary flow control valve 195. When the CPU 125 detects a substantial pressure build up in the output secondary manifold channel 395 by sampling the output of the secondary internal pressure sensor 225, the system 100 recognizes that the secondary output connector 400 is not engaged. When the secondary output connector 400 is engaged, the flap valve 230 is swung to an open engagement subjecting the output secondary manifold channel 395 to the pressure passed by the secondary control valve 195.

Logic circuitry 505 executed by the CPU 125 monitors and controls the operation of the insufflation system. The CPU 125 controls and monitors the insufflation gas flow rates and internal pressure of the gas delivery paths 270 and monitors the pressure in the intra-abdominal cavity though the separate sensing assembly 245. The CPU 125 is further programmed to monitor intra-abdominal pressure by sampling the output of one of two pressure-measuring transducers 155 and 160 when infusion gas is not flowing though the primary flow path 275. The logic circuitry 505 further provides a visual display 510, an RS 232 interface 515, a pressure select control 180, a flow limit control 185, and an audio alarm 520. The visual display 510 includes a display driver that is interfaced to the CPU 125. As illustrated in FIG. 2, the visual display 510 includes gas supply and over pressure LED indicators, a seven segment volume of gas used display, a seven segment flow control display, and a seven segment pressure display. The RS 232 interface 515 provides a multi-functional electronic interface to a wide variety of peripheral electronics and provides a calibration port that may be used to upgrade system software. The pressure select 180 and flow limit 185 controls are potentiometers that allow the user to select the maximum flow rate of the system from zero to thirty liters per minute and also select the maximum pressure from a range of zero to twenty-five millimeters of mercury. An audio alarm 520 is also interfaced to the controller 125 to alert the user to a variety of conditions that may include but are not limited to a low gas supply, a runaway flow rate, an over pressure condition, an open or obstructed gas delivery path, an open or obstructed internal sense line, and a loss of power.

Use of the system 100 will be described by referring to FIGS. 1 and 2 where it is assumed that the primary gas output channel 345 is the only gas output channel in use. First, the pressurized source of gas 105, the external output line 360, and the separate sense line 375 are connected to the system 100. The other end of the external output line 360 is connected to the patient's interior abdominal cavity. In making the connections to the patient's abdominal cavity, laparoscopic instruments having standard sizes can be used. For example, some standard laparoscopic instruments have gas passages in a range of approximately 0.065 inches to 0.123 inches.

After the proper connections are made, insufflating gas will begin passing through the common receiving channel 315, the primary branching channel 320 and the filter delivery channel 325. With the flap valve 230 closed, the pressure in the secondary flow path 280 will ramp up to the pressure defined by the static pressure relief valve 220. Gas penetration through the primary filter assembly 130 will depend upon the primary flow control valve's 135 aperture. As the system 100 is in a start-up condition, the aperture will be in an open and then closed position allowing the gas to flow in the "flow and stop" process. In the "flow and stop" process the system infuses insulating gas into the peritoneal cavity, allows the pressure to stabilize, and then the CPU 125 samples the output of one of two pressure-measuring transducers 155 and 160 until the surgeon determines that the separate sense line 375 should be connected. The separate sense line 375 is then connected to an unused trocar connector such as a Leur connector. To determine when the separate sense line 375 is properly connected, the CPU 125 will compare the static pressure sample at one of the pressure-measuring transducers 155 and 160 of the primary gas output channel 340 to the pressure sampled at the pressure-measuring transducer 175 connected to the separate sense line 170. When the external pressure measured in the separate sense line 170 equals the static pressure measured in the primary gas output channel 345 and the external pressure is greater than five millimeters of mercury, the system 100 will deliver a continuous or one-hundred percent duty cycle flow of insufflation gas to the intra-abdominal cavity. The gas infusion rate and pressure in the peritoneal cavity is then maintained by the CPU's control of the primary flow control valve 135 and the primary pressure relief valve 145.

Operation of the separate sensing assembly 245 is controlled by the flow of insufflation gas in the primary controlled flow path 246. When positive pressure builds up in the primary controlled flow path 246, a slight positive gas flows through the feed-flow orifice 165 and the feedback channels 365 and 370. The small flow of gas to the separate sense line 170 does not distort the pressure-measuring transducer's 175 accuracy. When the internal sense line is obstructed, however, the continuous small flow of gas into the separate sense line 170 causes a substantial increase in pressure in the separate sense line 170 inevitably equaling the pressure on the input junction of the feed-flow orifice 165. In this condition, the CPU's 125 sample of the pressure-measuring transducer's 175 output will alert the system 100 to the failure. The system 100 will revert to the "flow and stop" process and sample the intra-abdominal pressure by use of one of the primary and secondary pressure-measuring transducers 155, 225, and 160.

With the above described system, insufflating gas can be delivered continuously after the integrity of the sense line is confirmed. This enables greater flow rates to be delivered compared to a "stop-and-start" mode of operation. During delivery of insulating gas in continuous mode, the integrity of the sense line is monitored as described above. If the sense line becomes disconnected or obstructed, the controller responds by reverting to a "stop-and-start" mode of operation for gas delivery. When the controller again confirms the integrity of the sense line, continuous gas flow in the delivery path can be resumed. The controller can provide this function for each of the delivery paths.

II. Second Embodiment

Figure 3:
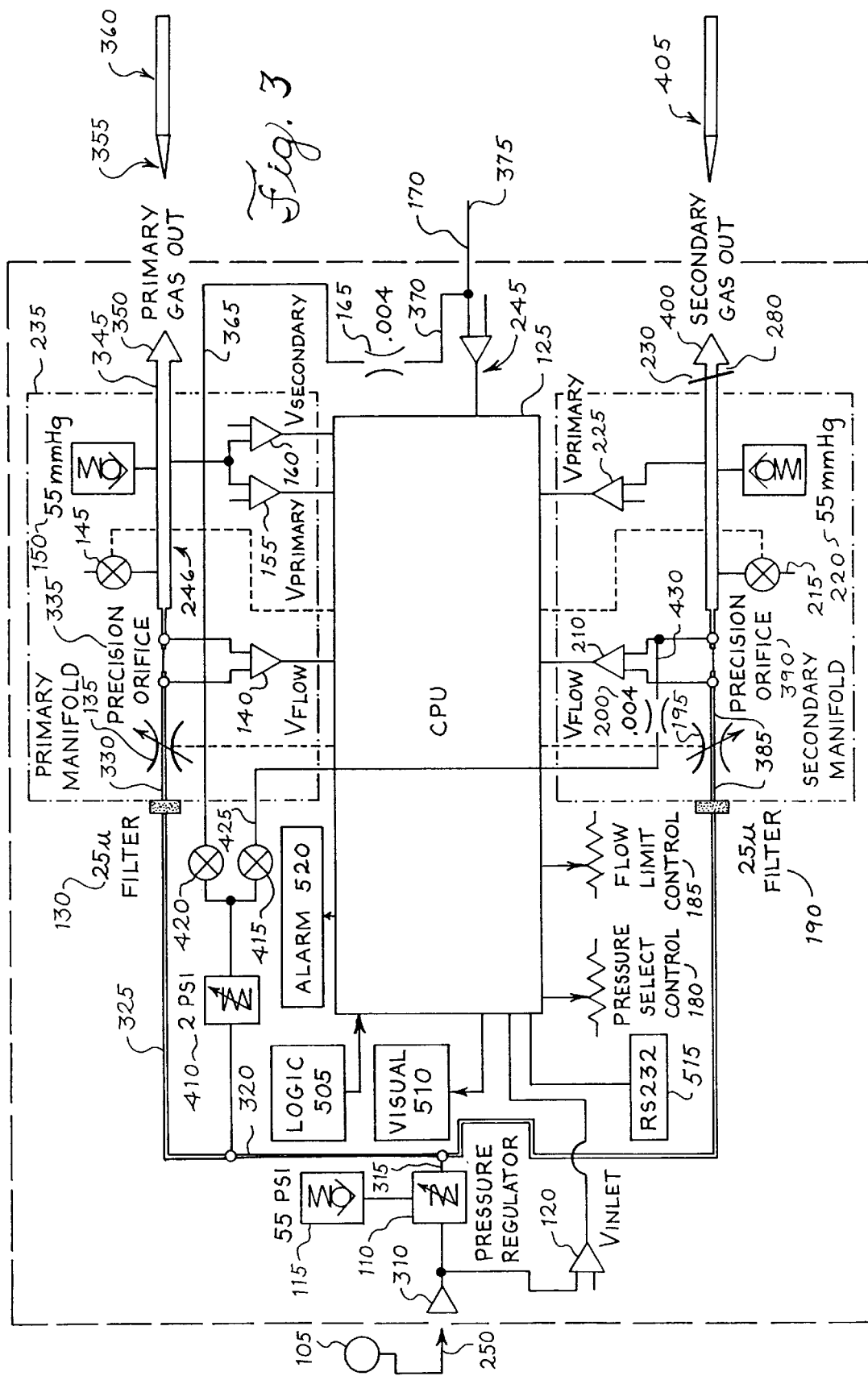
FIG. 3 is a diagram of a second embodiment of the improved laparoscopic insufflator.

A second embodiment of the multiple output port laparoscopic insufflator 100 is shown in FIG. 3. In this alternative configuration, the separate sensing assembly 245 is modified so that the feedback channels 365 and 370 provide a gas flow path from the primary branching channel 320 to the separate sense line 170. The feedback channel comprises the first feedback channel 365 and the second feedback channel 370. The first feedback channel 365 is joined to a digitally responsive primary control solenoid valve 420 at one end and to the input junction of the feed-flow orifice 165 at another end. The second feedback channel 370 is joined to the output junction of the feed-flow orifice 165 at one end and to the separate sense line 170 at another end.

The digitally responsive primary control solenoid valve 420 controls internal gas flow through the feedback channels 365 and 370. The CPU 125 communicates to the digitally responsive primary solenoid control valve 420 in response to the internal pressure measuring transducer 175. A static feedback pressure regulator 410 coupled to the primary branching channel 320 regulates feedback channels 365 and 370 pressure.

A low pressure channel 425 and 430 is created to provide a gas flow path from primary branching channel 320 to the secondary internal flow sensor 210. The low pressure channel comprises a first low pressure channel 425 and a second low pressure channel 430. The first low pressure channel 425 is joined to a digitally responsive secondary solenoid control valve 415 at one end and to the input junction of the bleed-off orifice 200 at another end. The second low pressure channel 430 is joined to the output junction of the of the bleed-off orifice 200 at one end and to the secondary internal flow sensor 210 at another end.

The digitally responsive secondary control solenoid valve 415 controls internal gas flow through the low pressure channel 425 and 430. The CPU 125 communicates to the digitally responsive secondary control solenoid valve 415 in response to the primary internal flow sensor 140. The static feedback pressure regulator 410 coupled to the primary branching channel 320 also regulates low pressure channel 425 and 430 pressure.

Operation of the modified separate sensing assembly 245 will be described by referring to FIGS. 1 and 3. When a static positive pressure above five millimeters of mercury is sensed by the pressure measuring transducers 175, the CPU 125 opens the primary solenoid control valve 420 to provide a two pounds per square inch gas flow through the feedback channels 365 and 370 and the feed-flow orifice 165. When a static pressure difference between the separate sense line 170 and the primary gas output channel 345 is less than three millimeters of mercury and the internal sensing line 170 pressure is greater than five millimeters of mercury, the system 100 delivers a continuous or one-hundred percent duty cycle flow of insufflation gas to the intra-abdominal cavity. When the separate sense line 170 is obstructed, however, the continuous flow of gas into the separate sense line 170 causes a substantial increase in pressure. In this condition, preferably when the pressure difference is greater than three millimeters of mercury, the CPU 125 alerts the system 100 to failure and reverts to the "flow and stop" process. Likewise, when the separate sense line 170 pressure drops below two millimeters of mercury, the system recognizes an "open condition," and reverts to the "flow and stop" process.

When only the primary gas output channel 345 is engaged in the second embodiment, the flap valve 230 is closed blocking the secondary gas output channel 281. When gas flow through the primary gas output channel 345 is flowing at a rate greater than four liters per minute, the CPU 125 opens the secondary solenoid control valve 415 to provide a two pounds per square inch gas flow through the low pressure channel 425 and 430 and the bleed-off orifice 200. The CPU 125 begins sampling the output of the secondary internal pressure sensor 225 five seconds after the CPU 125 opens the secondary solenoid control valve 415. The closure of the secondary gas output channel 281 causes a substantial pressure build up in the secondary gas output channel 281. When the CPU 125 detects a substantial pressure build up in the secondary gas output channel 281, by sampling the output of the secondary internal pressure sensor 225, the system 100 recognizes that the secondary output channel 281 is not engaged. When the secondary output channel 281 is engaged, the pressure difference between the primary and secondary pressure sensors 155, 160, and 225 must be within three millimeters of mercury before the system 100 delivers insufflating gas through the secondary gas output channel 281.

III. Third Embodiment

Figure 4:
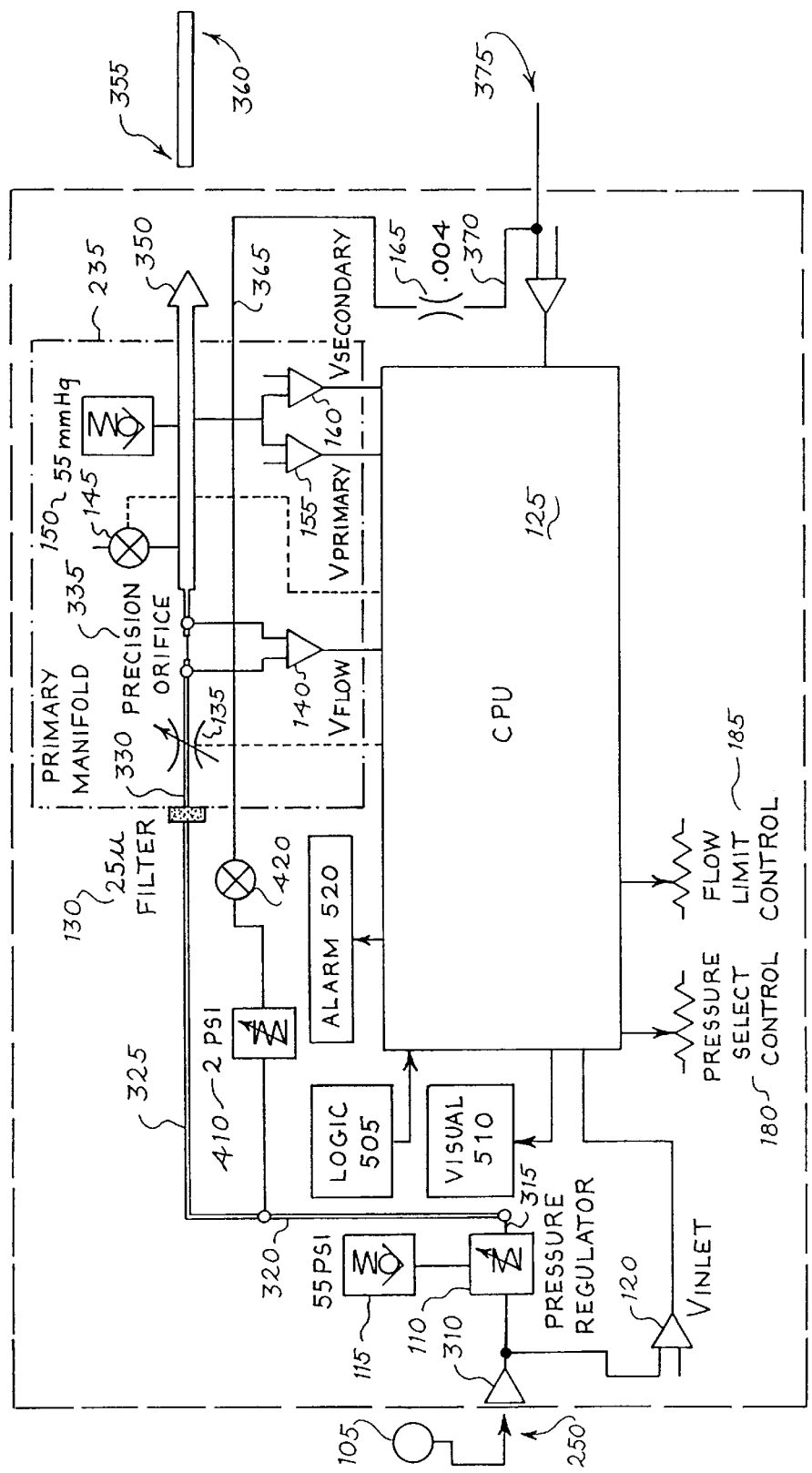
FIG. 4 is a diagram of a third embodiment of the improved laparoscopic insufflator.

FIG. 4 shows a third embodiment of the insulator. This third embodiment is similar in construction and operation to the embodiment shown in FIG. 3 with the exception that instead of having multiple gas supply lines, the insulator shown in FIG. 4 includes only a single gas delivery path 275. Like the previously described embodiments shown in FIGS. 1–3, the single gas supply line insufflator shown in FIG. 4 includes a sensing apparatus 245 that connects to a separate sense line 170. Using the separate sense line 375, and the logic circuitry 505 that implements measurements using the sense line and supply line during insufflation, the embodiment of FIG. 4 provides advantages that are similar to those provided by the first and second embodiments. Specifically, by using the separate sense line 170, the gas delivery path 275 can be operated at, or close to, a 100% duty cycle. Thus, the embodiment of FIG. 4 provides advantages over conventional insufflators that alternate periods of gas delivery with static measurement periods. Relative to the embodiments shown in FIGS. 1 and 3, the insufflator shown in FIG. 4 would provide a lower overall flow because it has only a single supply line compared to the multiple supply lines shown in the embodiments of FIGS. 1 and 3.

IV. Exemplary Components

The concepts and processes previously illustrated may be implemented through hardware, software, and logic circuitry. The aforementioned embodiments may be constructed from a variety of commercially available components including:

| Component: | available from: |
|---|---|
| safety relief valve 115 | Circle Seal Controls in Anaheim, CA |
| pressure relief valves 145 and 215 | Parker Hannifin Corp. in Rollis, NH |
| static pressure relief valve 150, and 220 | Halkey-Roberts Corp. in St. Petersburg, FL |
| flow control valve or proportional valve 135 and 195 | Parker Hannifin Corp. in Rollis, NH |
| differential flow-measuring transducer 140 and 210 | IC Sensors in Milpitas, CA |
| separate sense line 170 | PVC tubing having an outside diameter of .110 inches, an inside diameter of .050 inches Applied Plastics in Oak Creek, WI |
| standard male and female Luer connector | from Haemotronics, Inc. in Newark NJ |
| a feed-flow orifice 165 and 200 having an inside diameter of .004 inches | Air Control in Racine, WI |
| primary and secondary external output line 360 and 405 having an inside diameter of .250 inches | Applied Plastics in Oak Creek, WI |
| octal bus transmitter/receiver I.C. 74LS245 | Motorola |
| eight-bit microprocessor I.C. 8032 | Intel |
| instrumentation amplifier I.C. AD 620 | Analog Devices in Norwood, Maryland |
| dual operational amplifier I.C. LM358 | Texas Instruments in Dallas, Texas |
| a twelve bit analog to digital converter I.C. Max 199 | Maxim Integrated Products in Sunnyvale, CA |
| 8K byte EPROM 27C256 | Texas Instruments in Dallas, Texas |
| programmable logic device GAL 22V10 | from Lattice Semiconductor |
| 256 byte EEPROM 24CO2 | Thomson |

V. Advantages

In accordance with the disclosed embodiments, an insufflation system, apparatus, and method 100 for performing safe laparoscopy is disclosed. The disclosed embodiment provides a system, apparatus, and method 100 capable of providing continuity between the separate sense line 170 and the intra-abdominal cavity, facilitates static and continuous pressure measurements, provides a continuous or flow stop infusion gas flow, and is capable of detecting blocked or inadvertently disconnected gas output lines. The disclosed embodiments enjoy utility in any laparoscopic surgical environment. The system 100, for example, may be interfaced to other electronic devices through its RS232 port 515 to create a fully integrated electronic laparoscopic environment.

The present disclosure departs from the conventional insufflation art by integrating systems that detect failure conditions. Typical laparoscopic operations rely on gas delivery tubes, flow rate controllers, and pressure sensing transducers to control insulation flow rate and sense intra-abdominal pressure. The conventional art employs sensors that are hollow pieces of tubing connected between the interior abdominal cavity and a pressure sensing transducer unencumbered by any gas flow. The conventional art shuns the use of positive gas flow in pressure-measuring lines, primarily because of a fear that any gas flow would affect the accuracy of any pressure measurement.

The present disclosure proceeds against the conventional art in at least two respects. In an embodiment of the present disclosure, a slight positive gas flows from a pressure regulator 410 and passes through a separate sense line 170 that vents to the intra-abdominal cavity. By delivering a small flow rate of gas through the separate sense line 375, the pressure-measuring transducer 175 is subject to minimal or low distortion. However, unlike conventional insufflators, the continuous positive flow of gas through the separate sense line 170 causes a substantial increase in pressure when the internal sense line 375 is obstructed. In an open failure condition, the continuous flow of gas through the separate sense line 170 is vented. In this condition, a comparison of pressures measured at the separate sense line 170 and the primary gas output line 345 are analyzed. A substantial difference in pressure identifies an open condition.

In another preferred aspect of an embodiment, a secondary gas delivery path 280 would include an automatic flap valve 230 located between the secondary gas output connector 400 and the secondary gas output channel 281. In normal operation, the closure of the automatic flap valve 230 causes a substantial pressure build up in the secondary gas output channel 281. Substantial pressure in the secondary gas output channel 281 indicates that the secondary delivery path 280 is not in use.

Variations and modifications of the embodiments disclosed herein may be made without departing from scope and spirit of the invention. The aforementioned description is intended to be illustrative rather than limiting and it is understood that the scope of the invention is set forth by the following claims.

I claim:

1. An insufflation system for use with laparoscopic surgical equipment comprising:
    a delivery assembly for delivering insufflating gas from a pressurized source of insufflating gas to at least one gas delivery path and a separate sensing line that are connectable to a laparoscopic surgical equipment that is insertable into a peritoneal cavity;
    a separate sensing assembly connected to said separate sensing line; and
    a controller coupled to said delivery assembly and said separate sensing assembly,
    wherein said controller monitors said separate sensing assembly to confirm absence of leakage in said separate sensing line and unobstructed connection of said separate sensing line to said peritoneal cavity,
    and further wherein said controller provides for continuous delivery of insufflating gas via said delivery assembly upon said confirming and otherwise provides for non-continuous delivery of insufflating gas via said delivery assembly.

2. The insufflation system of claim 1, wherein said separate sensing assembly continuously monitors pressure within said peritoneal cavity.

3. The insufflation system of claim 1, wherein said insufflating gas is delivered first at a periodic rate and then at a continuous rate.

4. The insufflation system of claim 1 further comprising an active pressure control valve and a passive pressure control valve, wherein said active pressure control valve is responsive to said controller and said passive pressure control valve is responsive to the pressure of said delivery assembly.

5. The insufflation system of claim 1 further comprising a flap valve interposed between said delivery assembly and said at least one gas delivery path.

6. The insufflation system of claim 1, wherein said separate sensing assembly includes an orifice.

7. The insufflation system of claim 6, wherein said orifice has a diameter of not more than 0.004 inches.

8. The insufflation system of claim 1, wherein said separate sensing assembly includes an orifice interposed within a feedback path that connects said at least one delivery path to said separate sensing line.

9. The insufflation system of claim 1, wherein said separate sensing assembly includes at least one pressure measuring device.

10. The insulation system of claim 1, wherein said separate sensing assembly includes at least one pressure measuring device in communication with said controller.

11. The insufflation system of claim 1, wherein said delivery assembly delivers insufflating gas from said pressurized source to more than one of said at least one gas delivery path, said delivery assembly further comprising a plurality of flow control valves capable of providing independent gas flow rates to said more than one gas delivery paths.

12. The insufflation system of claim 1, wherein said delivery assembly delivers insufflating gas from said pressurized source to a primary gas delivery path and at least one secondary gas delivery path, wherein said at least one secondary gas delivery path channels a continuous flow of gas and has a separate flap valve that in a closed position blocks said at least one secondary gas delivery path and alerts said system that said at least one secondary gas delivery path is not in use.

13. The insufflation system of claim 12, wherein the closure of said flap valve causes a pressure build up in said at least one secondary gas delivery path that is identified by said controller.

14. An insufflation apparatus, comprising:
a plurality of delivery channels that define a gaseous flow path from a pressurized source of insufflating gas to at least one trocar assembly and a separate sensing line, wherein said trocar assembly and said separate sensing line are insertable into an internal body cavity;
a plurality of pressure regulating valves interposed between said pressurized source of insufflating gas and said trocar assembly;
a separate sensing assembly connected to said separate sensing line for monitoring internal body pressure and assuring continuity from said internal body cavity through said separate sensing line, and
a controller coupled to said delivery channels, said pressure regulating valves, and said separate sensing assembly to control insufflation pressure and gas flow rate, wherein said controller provides for continuous delivery of insufflating gas upon absence of leakage in said separate sensing line and unobstructed connection of said separate sensing line to said internal body cavity and otherwise provides for non-continuous delivery of insufflating gas.

15. The insufflation apparatus according to claim 14 further comprising a variable valve responsive to said controller to regulate said gas flow rate.

16. The insufflation apparatus according to claim 14 wherein said controller allows a continuous infusion of insufflating gas into said internal body cavity.

17. The insufflation apparatus according to claim 14, wherein at least one of said pressure regulating valves is responsive to said controller and at least one of said plurality of pressure regulating valves is responsive to the pressure of said delivery channels.

18. The insufflation apparatus according to claim 14 further comprising operator controlled pressure select and flow rate controls interfaced to said controller.

19. The insufflation apparatus according to claim 14 further comprising at least one visual and audio display interfaced to said controller.

20. The insufflation apparatus according to claim 14, wherein said controller is a programmable micro-controller interfaced to a memory responsive to manual and automatic control.

21. An insufflation apparatus comprising:
a plurality of delivery channels that define a gaseous flow path from a pressurized source of insulating gas to at least one trocar assembly and a separate sensing line, wherein said trocar assembly and said separate sensing line are insertable into an internal body cavity;
a plurality of pressure regulating valves interposed between said pressurized source of insulating gas and said trocar assembly;
a separate sensing assembly connected to said separate sensing line for monitoring internal body pressure and assuring continuity from said internal body cavity through said separate sensing line;
a controller coupled to said delivery channels, said pressure regulating valves, and said separate sensing assembly to control insufflation pressure and gas flow rate; and
a differential flow rate sensor interposed between said pressurized source of insufflating gas and said internal assembly to monitor said gas flow rate in said delivery channels.

22. An insufflation device, comprising:
means for delivering insufflating gas from a pressurized source to at least one delivery path coupled to a separate sensing line that are insertable into a peritoneal cavity;
means for monitoring peritoneal pressure and sensing continuity from said peritoneal cavity through said separate sensing line; and
means for controlling insulation pressure and gas flow rate.

23. A method comprising the steps of:
providing an insufflation system capable of providing a first periodic flow and then a continuous flow of insufflating gas into a peritoneal cavity through a delivery line and a separate sensing line to achieve pneumoperitoneum;
sensing a difference between a pressure within said peritoneal cavity and a pressure of said insufflating gas continuously by comparing the pressures of said delivery line and said sensing line.

24. A process for achieving pneumoperitoneum comprising the steps of:
inserting a delivery line and a separate sensing line into an internal body cavity;
infusing an insufflating gas through said delivery line and said separate sensing line to insufflate said internal body cavity;
measuring a pressure of said insufflating gas through said delivery line and said separate sensing line;
comparing said pressure of said insufflating gas through said delivery line and said separate sensing line; and then
controlling gas infusion rates into said internal body cavity and pressure in said internal body cavity in response to said comparing said pressure of said insufflating gas.

25. An insulation system, comprising:
a delivery assembly for delivering insufflating gas from a pressurized source to at least one gas delivery path and a separate sensing line that are insertable into a peritoneal cavity;

an internal sensing assembly connected to said separate sensing line through a first control valve; and a controller coupled to said delivery assembly and said first control valve to control insufflation pressure and gas flow rates, wherein said controller provides for continuous delivery of insufflating gas upon absence of leakage in said separate sensing line and unobstructed connection of said separate sensing line to said peritoneal cavity and otherwise provides for non-continuous delivery of insufflating gas.

26. The insufflation system of claim 25 wherein said first control valve is responsive to said controller.

27. The insufflation system of claim 25 further comprising a passive pressure control valve interposed between said at least one gas delivery path and said first control valve, wherein said passive pressure control valve is responsive to pressure of said at least one gas delivery path.

28. The insufflation system of claim 25, wherein said delivery assembly delivers insufflating gas from said pressurized source to a primary gas delivery path and at least one secondary gas delivery path, wherein said at least one secondary gas delivery path has a separate flap valve that in a closed position blocks said at least one secondary gas delivery path and alerts said system that said at least one secondary gas delivery path is not in use.

29. The insufflation system of claim 28, further comprising at least a second control valve interposed between said primary gas delivery path and an orifice coupled to said at least one secondary gas delivery path.

30. The insufflation system of claim 29, comprising a passive pressure control valve interposed between said gas delivery path and said first and second control valves, wherein said passive pressure control valve is responsive to the pressure of said primary gas delivery path and said first and said second control valves are responsive to said controller.

31. An insufflation system, comprising:

a delivery assembly for delivering insufflating gas from a pressurized source to at least one gas delivery path and a separate sensing line that are insertable into a peritoneal cavity;

an internal sensing assembly connected to said separate sensing line through a first control valve;

a controller coupled to said delivery assembly and said first control valve to control insufflation pressure and gas flow rates; and wherein said internal sensing assembly includes an orifice interposed within a feedback path that connects said gas delivery path to said separate sensing line.

32. The insufflation system of claim 31, wherein said orifice has a diameter of not more than 0.004 inches.

33. An insufflation system for use with laparoscopic instruments having gas passages in a range of approximately 0.065 inches to 0.123 inches, the insufflation system comprising:

a delivery assembly for delivering insufflating gas from a pressurized source of insufflating gas to a plurality of gas delivery paths and a separate sensing line that are insertable into a peritoneal cavity, and wherein said plurality of gas delivery paths have a total flow of approximately at least 40 liters per minute;

a separate sensing assembly connected to said separate sensing line; and a controller coupled to said delivery assembly and said separate sensing assembly, wherein said controller monitors said separate sensing assembly and provides for delivery of insufflating gas via said delivery assembly up to at least approximately 40 liters per minute, wherein said controller provides for continuous delivery of insufflating gas upon absence of leakage in said separate sensing line and unobstructed connection of said separate sensing line to said peritoneal cavity and otherwise provides for non-continuous delivery of insufflating gas.

34. An insufflation apparatus, comprising:

a plurality of delivery channels that define a gaseous flow path from a pressurized source of insufflating gas to at least one trocar assembly and a separate sensing line, wherein said trocar assembly and said separate sensing line are insertable into an internal body cavity;

a plurality of pressure regulating valves interposed between said pressurized source of insufflating gas and said trocar assembly;

a separate sensing assembly connected to said separate sensing line for monitoring internal body pressure and assuring continuity from said internal body cavity through said separate sensing line, and a controller coupled to said delivery channels, said pressure regulating valves, and said separate sensing assembly to control insufflation pressure and gas flow rate, wherein said controller confirms absence of leakage in said separate sensing line and unobstructed connection of said separate sensing line to said internal body cavity.

35. The insufflation apparatus according to claim 34 further comprising a variable valve responsive to said controller to regulate said gas flow rate.

36. The insufflation apparatus according to claim 34, further comprising a differential flow rate sensor interposed between said pressurized source of insufflating gas and said internal assembly to monitor said gas flow rate in said delivery channels.

37. The insufflation apparatus according to claim 34 wherein said controller allows a continuous infusion of insufflating gas into said internal body cavity.

38. The insufflation apparatus according to claim 34, wherein at least one of said pressure regulating valves is responsive to said controller and at least one of said plurality of pressure regulating valves is responsive to the pressure of said delivery channels.

39. The insufflation apparatus according to claim 34 further comprising operator controlled pressure select and flow rate controls interfaced to said controller.

40. The insufflation apparatus according to claim 34 further comprising at least one visual and audio display interfaced to said controller.

41. The insufflation apparatus according to claim 34, wherein said controller is a programmable micro-controller interfaced to a memory responsive to manual and automatic control.

42. An insufflation system, comprising:

a delivery assembly for delivering insufflating gas from a pressurized source to at least one gas delivery path and a separate sensing line that are insertable into a peritoneal cavity;

an internal sensing assembly connected to said separate sensing line through a first control valve; and a controller coupled to said delivery assembly and said first control valve to control insufflation pressure and gas flow rates, wherein said controller confirms absence of leakage in said separate sensing line and unobstructed connection of said separate sensing line to said peritoneal cavity.

43. The insufflation system of claim 42 wherein said first control valve is responsive to said controller.

44. The insufflation system of claim 42 further comprising a passive pressure control valve interposed between said at least one gas delivery path and said first control valve, wherein said passive pressure control valve is responsive to pressure of said at least one gas delivery path.

45. The insufflation system of claim 42, wherein said internal sensing assembly includes an orifice interposed within a feedback path that connects said gas delivery path to said separate sensing line.

46. The insufflation system of claim 45, wherein said orifice has a diameter of not more than 0.004 inches.

47. The insufflation system of claim 42, wherein said delivery assembly delivers insufflating gas from said pressurized source to a primary gas delivery path and at least one secondary gas delivery path, wherein said at least one secondary gas delivery path has a separate flap valve that in a closed position blocks said at least one secondary gas delivery path and alerts said system that said at least one secondary gas delivery path is not in use.

48. The insufflation system of claim 47, further comprising at least a second control valve interposed between said primary gas delivery path and an orifice coupled to said at least one secondary gas delivery path.

49. The insufflation system of claim 48, comprising a passive pressure control valve interposed between said gas delivery path and said first and second control valves, wherein said passive pressure control valve is responsive to the pressure of said primary gas delivery path and said first and said second control valves are responsive to said controller.

50. An insufflation system for use with laparoscopic instruments having gas passages in a range of approximately 0.065 inches to 0.123 inches, the insufflation system comprising:

a delivery assembly for delivering insufflating gas from a pressurized source of insufflating gas to a plurality of gas delivery paths and a separate sensing line that are insertable into a peritoneal cavity, and wherein said plurality of gas delivery paths have a total flow of approximately at least 40 liters per minute;

a separate sensing assembly connected to said separate sensing line; and a controller coupled to said delivery assembly and said separate sensing assembly, wherein said controller monitors said separate sensing assembly and provides for delivery of insufflating gas via said delivery assembly up to at least approximately 40 liters per minute, wherein said controller confirms absence of leakage in said separate sensing line and unobstructed connection of said separate sensing line to said peritoneal cavity.

* * * * *

UNITED STATES PATENT AND TRADEMARK OFFICE
CERTIFICATE OF CORRECTION

PATENT NO.    : 6,299,592 B1
DATED         : October 9, 2001
INVENTOR(S)   : Charles Zander It is certified that error appears in the above-identified patent and that said Letters Patent is hereby corrected as shown below:

Column 12,
Line 5, immediately after "apparatus" insert -- , -- (comma).
Lines 7 and 12, delete "insulating" and substitute -- insufflating -- in its place.
Line 36, delete "insulation" and substitute -- insufflation -- in its place.
Line 65, delete "insulation" and substitute -- insufflation -- in its place.

Signed and Sealed this

Twenty-fourth Day of September, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

| | |
|---|---|
| PATENT NO. | : 6,299,592 B1 |
| APPLICATION NO. | : 09/173810 |
| DATED | : October 9, 2001 |
| INVENTOR(S) | : Charles Zander |

It is certified that error appears in the above-identified patent and that said Letters Patent is hereby corrected as shown below:

In the Claims

In column 11, claim 10, line 8, replace "The insulation system" with --The insufflation system--.

Signed and Sealed this
Twenty-fourth Day of September, 2013

Teresa Stanek Rea
*Deputy Director of the United States Patent and Trademark Office*